US012611135B2

(12) United States Patent
Dang et al.

(10) Patent No.: US 12,611,135 B2
(45) Date of Patent: Apr. 28, 2026

(54) TRAUMATIC EVENT DETECTION

(71) Applicant: INTERNATIONAL BUSINESS MACHINES CORPORATION, Armonk, NY (US)

(72) Inventors: Bing Dang, Chappaqua, NY (US); Bo Wen, New York, NY (US); Tian Hao, White Plains, NY (US); Jeffrey L. Rogers, Briarcliff Manor, NY (US); Erhan Bilal, Westport, CT (US)

(73) Assignee: International Business Machines Corporation, Armonk, NY (US)

( * ) Notice: Subject to any disclaimer, the term of this patent is extended or adjusted under 35 U.S.C. 154(b) by 1013 days.

(21) Appl. No.: 17/690,297

(22) Filed: Mar. 9, 2022

(65) Prior Publication Data

US 2023/0284965 A1     Sep. 14, 2023

(51) Int. Cl.
| | |
|---|---|
| *A61B 5/00* | (2006.01) |
| *A61B 5/0205* | (2006.01) |
| *A61B 5/024* | (2006.01) |
| *A61B 5/0531* | (2021.01) |
| *G16H 10/20* | (2018.01) |

(52) U.S. Cl.
CPC .......... *A61B 5/4088* (2013.01); *A61B 5/0205* (2013.01); *A61B 5/024* (2013.01); *A61B 5/0531* (2013.01); *A61B 5/4064* (2013.01); *A61B 5/6802* (2013.01); *A61B 5/7221* (2013.01); *G16H 10/20* (2018.01)

(58) Field of Classification Search
CPC ..... A61B 5/4088; A61B 5/0205; A61B 5/024; A61B 5/0531; A61B 5/4064; A61B 5/6802; A61B 5/7221; G16H 10/20
See application file for complete search history.

(56) References Cited

U.S. PATENT DOCUMENTS

| | | | |
|---|---|---|---|
| 10,182,746 B1 * | 1/2019 | Demiralp | A61B 5/1118 |
| 11,049,605 B1 * | 6/2021 | Peters | G16H 20/70 |
| 2010/0234717 A1 | 9/2010 | Wismer | |
| 2015/0245795 A1 * | 9/2015 | Rennaker | G01P 15/135 600/595 |
| 2015/0287960 A1 | 10/2015 | Andry | |

(Continued)

FOREIGN PATENT DOCUMENTS

| | | |
|---|---|---|
| CN | 107532959 B | 6/2020 |
| KR | 20170140090 A | 12/2017 |

OTHER PUBLICATIONS

Anonymous, "Smart Watch Integration with Smart Contact Lens Casing," IP.com No. IPCOM000261673D, IP.com Electronic Publication Date: Mar. 26, 2020, pp. 1-6.

(Continued)

*Primary Examiner* — Justin Xu
*Assistant Examiner* — Jonathan M Haney
(74) *Attorney, Agent, or Firm* — Kristofer Haggerty

(57) ABSTRACT

A method, a structure, and a computer system for traumatic event detection. The exemplary embodiments may include collecting data using sensors worn by a user and identifying a traumatic event based on applying a model to the data, wherein the model correlates values of the data with traumatic events and traumatic brain injuries. The exemplary embodiments may further include identifying the traumatic brain injury resulting from the traumatic event.

17 Claims, 5 Drawing Sheets

(56)          References Cited

U.S. PATENT DOCUMENTS

| | | | | |
|---|---|---|---|---|
| 2016/0073945 | A1* | 3/2016 | Fine | G16Z 99/00 |
| | | | | 600/558 |
| 2016/0097756 | A1 | 4/2016 | Borkholder | |
| 2016/0213300 | A1* | 7/2016 | Allen | A61B 5/4064 |
| 2016/0278684 | A1 | 9/2016 | Kozloski | |
| 2016/0331295 | A1 | 11/2016 | Kozloski | |
| 2017/0042480 | A1 | 2/2017 | Gandhi | |
| 2017/0086668 | A1 | 3/2017 | Francois | |
| 2021/0107501 | A1 | 4/2021 | Monteil | |

OTHER PUBLICATIONS

Ku et al., "Smart, soft contact lens for wireless immunosensing of cortisol," Science Advances, vol. 6, No. 28, Jul. 8, 2020: eabb2891, pp. 1-10.
Mell et al., "The NIST Definition of Cloud Computing", National Institute of Standards and Technology, Special Publication 800-145, Sep. 2011, pp. 1-7.
Stephens, Physics World, "For concussions, the eyes are windows to the brain," Apr. 30, 2020 [Accessed Aug. 18, 2021], https://physicsworld.com/a/for-concussions-the-eyes-are-windows-to-the-brain/, pp. 1-4.

* cited by examiner

Figure 3:
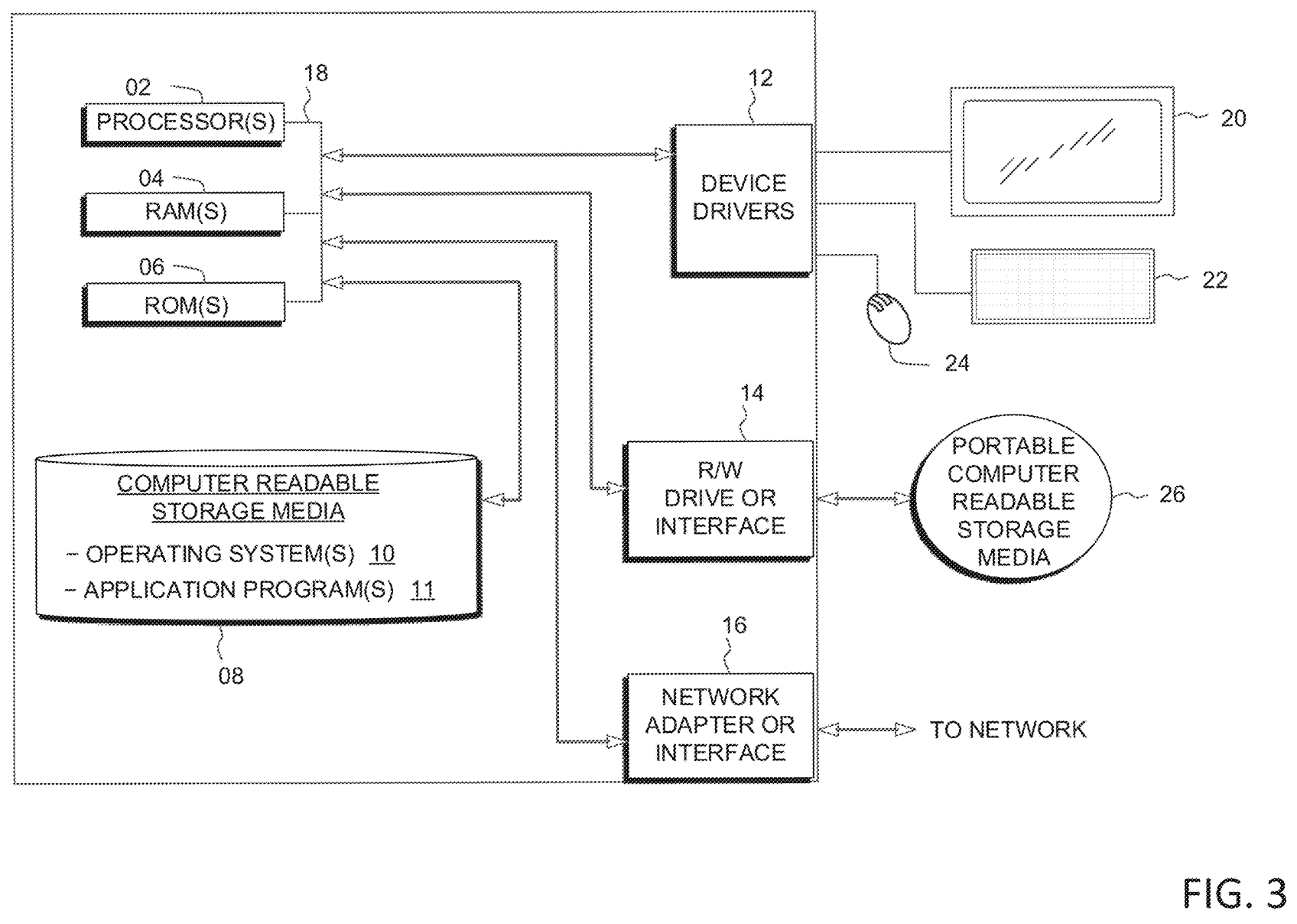

PORTABLE COMPUTER READABLE STORAGE MEDIA

TO NETWORK

12

DEVICE DRIVERS

14

R/W DRIVE OR INTERFACE

16

NETWORK ADAPTER OR INTERFACE

18

02 PROCESSOR(S)

04 RAM(S)

06 ROM(S)

COMPUTER READABLE STORAGE MEDIA

– OPERATING SYSTEM(S) 10

– APPLICATION PROGRAM(S) 11

08

TRAUMATIC EVENT DETECTION

BACKGROUND

The exemplary embodiments relate generally to traumatic event detection, and more particularly to identifying traumatic events and traumatic brain injuries via wearable devices.

Traumatic brain injury (TBI) is a sudden injury that causes damage to the brain. It may happen when there is a blow, bump, or jolt to the head, for example in traumatic events such as a car crash, intensive sport, natural disaster, etc. When a traumatic event that may cause TBI occurs, it is important to diagnose TBI as quickly as possible, however this may prove difficult without understanding a context of the traumatic event.

SUMMARY

The exemplary embodiments disclose a method, a structure, and a computer system for traumatic event detection. The exemplary embodiments may include collecting data using sensors worn by a user and identifying a traumatic event based on applying a model to the data, wherein the model correlates values of the data with traumatic events and traumatic brain injuries. The exemplary embodiments may further include identifying the traumatic brain injury resulting from the traumatic event.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which:

FIG. 3 depicts an exemplary block diagram depicting the hardware components of the traumatic event detection system 100 of FIG. 1, in accordance with the exemplary embodiments.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
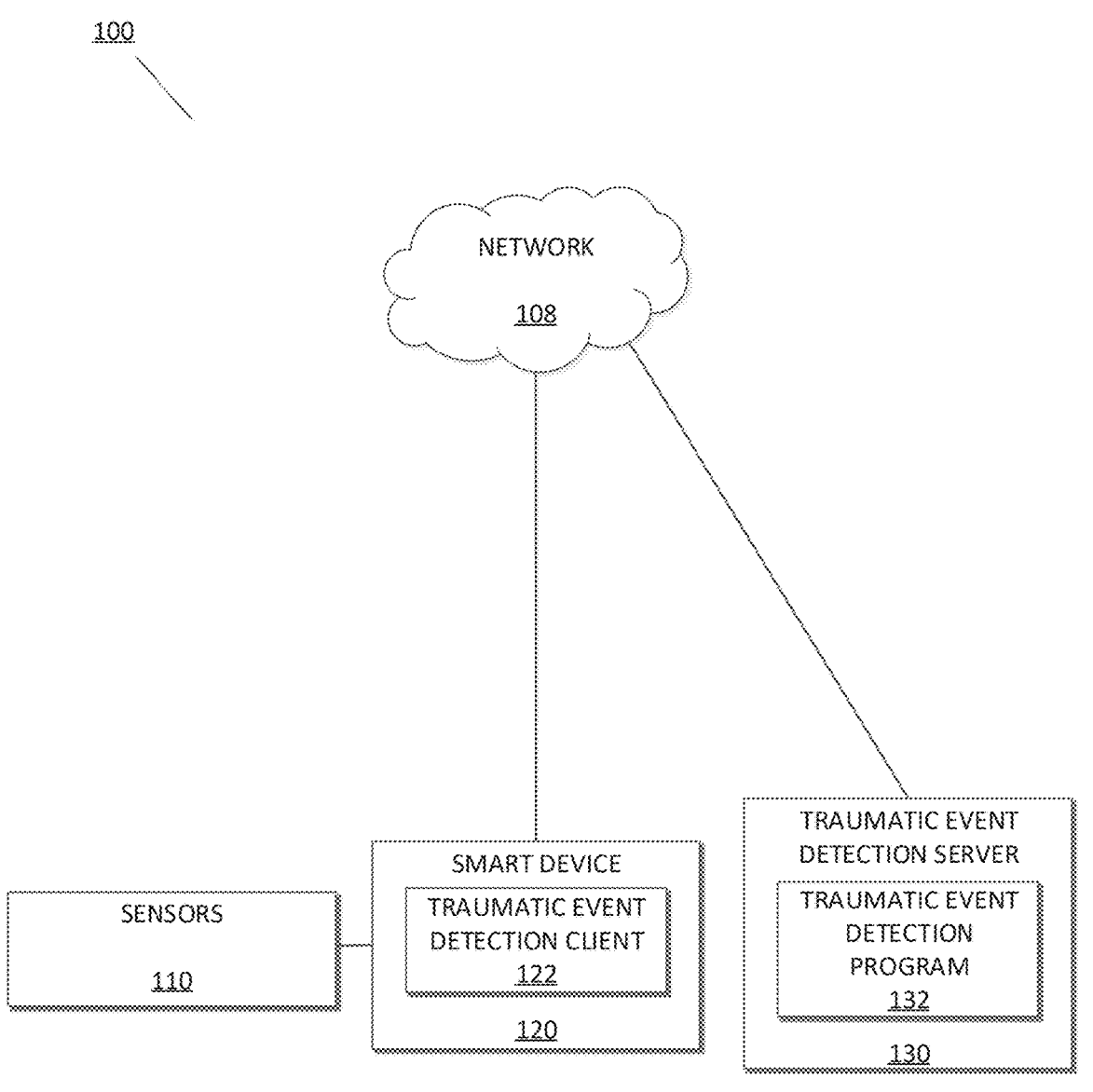
FIG. 1 depicts an exemplary schematic diagram of a traumatic event detection system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

Traumatic brain injury (TBI) is a sudden injury that causes damage to the brain. It may happen when there is a blow, bump, or jolt to the head, for example in traumatic events such as a car crash, intensive sport, natural disaster, etc. When a traumatic event that may cause TBI occurs, it is important to diagnose TBI as quickly as possible, however this may prove difficult without understanding a context of the traumatic event.

The present invention solves the aforementioned problem of identifying a source and a magnitude of traumatic events, as well as diagnoses TBJ. The present invention may do so using one or more worn or implanted sensors, e.g., a smart contact lens, a smart earplug, and a smart adhesive patch, used in conjunction with a program capable of analyzing measurements made by the one or more sensors. The present invention will detect events with different intrinsic time scales, beginning with the overpressure wave that may be supersonic and require detection of 10 microseconds (10 μs) variations. Those events and signals with slower timescales associated with any debris or acceleration will then also be recorded. The invention may be capable of sensing directionality, and may measure an eye stress, e.g., at ~1 megahertz (1 MHz). Perhaps most importantly, the present invention may assess the impact to personal well-being very quickly, allowing for rapid medical treatment. Detailed description of the invention follows.

FIG. 1 depicts the traumatic event detection system 100, in accordance with exemplary embodiments. According to the exemplary embodiments, the traumatic event detection system 100 may include one or more sensors 110, a smart device 120, and a traumatic event detection server 130, which all may be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted. The operations of the mobility assessment system 100 are described in greater detail herein.

In the exemplary embodiments, the network 108 may be a communication channel capable of transferring data between connected devices. In the exemplary embodiments, the network 108 may be the Internet, representing a world-wide collection of networks and gateways to support communications between devices connected to the Internet. Moreover, the network 108 may utilize various types of connections such as wired, wireless, fiber optic, etc., which may be implemented as an intranet network, a local area network (LAN), a wide area network (WAN), a combination thereof, etc. In further embodiments, the network 108 may be a Bluetooth network, a Wi-Fi network, a combination thereof, etc. The network 108 may operate in frequencies including 2.4 gHz and 5 gHz internet, near-field communication, etc. In yet further embodiments, the network 108 may be a telecommunications network used to facilitate telephone calls between two or more parties comprising a landline network, a wireless network, a closed network, a satellite network, a combination thereof, etc. In general, the network 108 may represent any combination of connections and protocols that will support communications between connected devices.

In exemplary embodiments, the sensors 110 may be one or more devices, e.g., wearable devices or implanted devices, capable of collecting data. In particular, the sensors 110 may be configured to collect data that may be analysed to detect a traumatic event, including environmental data such as light, overpressure, sound, acceleration, stress, strain, etc., as well as biometric data such as pulse O2, heart rate, respiration, skin conductivity, pH, etc. The sensors 110 may further collect data relating to the cognitive response, e.g., through voice, drawing, or a questionnaire/survey. Accordingly, the sensors 110 may be a wearable smart device (e.g., a smart contact lens, a smart earplug, a smart watch, a smart adhesive patch, smart clothing, etc.) or an implant that includes any one or more of a light sensor, camera, microphone, accelerometer, barometer/pressure sensor, strain gauge, pulse oximetry sensor, heartrate monitor, respiration monitor, skin conductance sensor, pH sensor, etc. For example, the present invention may implement micro-electromechanical systems-based (MEMS-based) ultrafast switches that can respond to light intensity and high-pressure waves within 10 µs.

Figure 4:
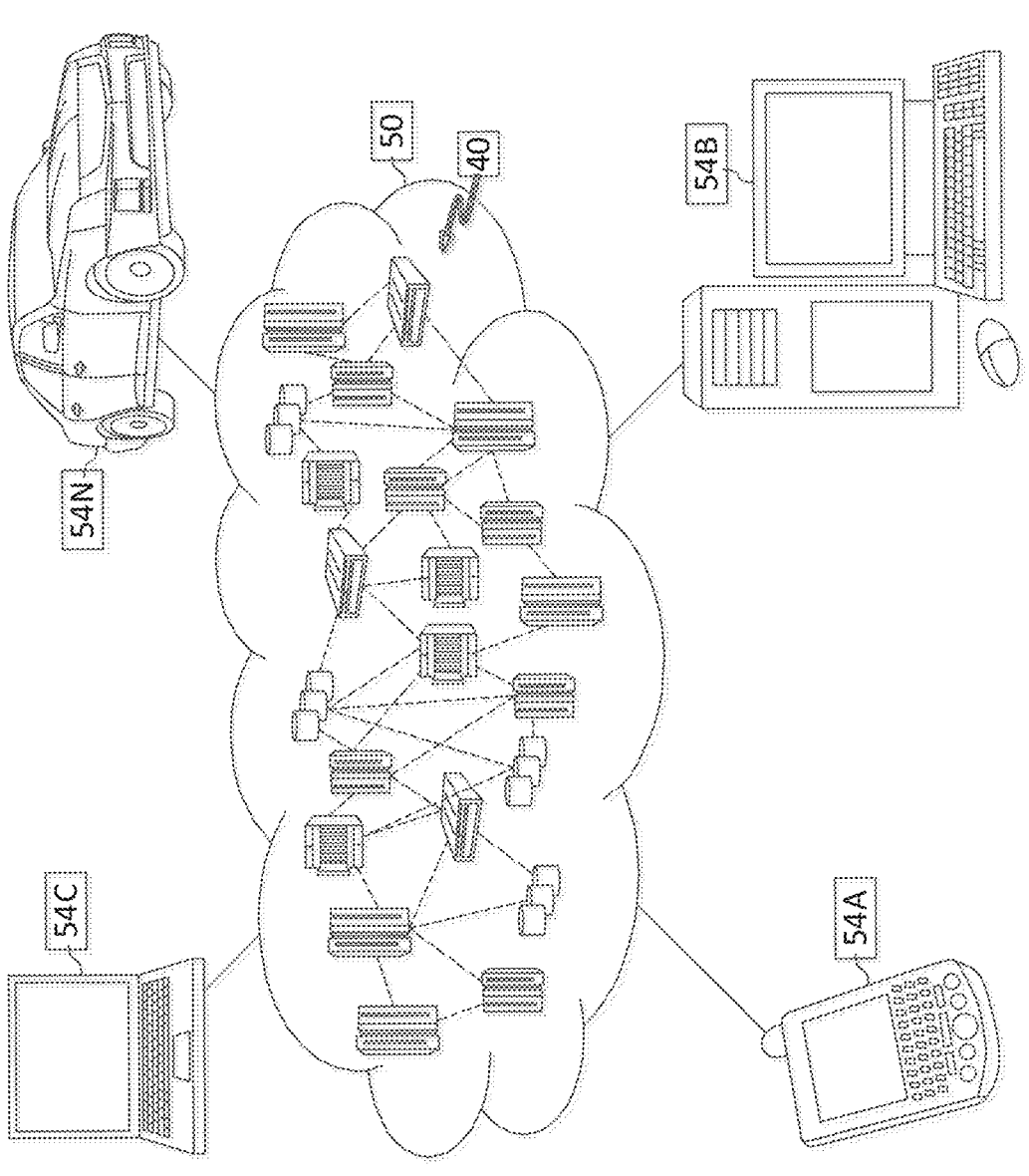
FIG. 4 depicts a cloud computing environment, in accordance with the exemplary embodiments.

In embodiments, the sensors 110 may further include a memory, wireless adapter (e.g., low power radio frequency), Global Positioning System (GPS) transceiver, gyroscope, and other components illustrated by FIG. 4. An onboard image sensor and memory can record a video for longer than 1 sec upon activation and low-power radio frequency (RF) wireless communication can be established to transmit the data for >1 sec upon activation. The sensors 110 may communicate with the network 108 or with the smart device 120 through means such as WiFi, Bluetooth, Near Field Communication (NFC), etc. Such communication may allow for the sensors 110 to each report measurements to a central hub located in, on, or near the body, e.g., the smart device 120. In general, the sensors 110 may be any device capable of collecting data relating to atmospheric/environmental factors and wearer biometrics. The sensors 110 are described in greater detail with respect to FIG. 2-5.

In exemplary embodiments, the smart device 120 includes a traumatic event detection client 122, and may be an enterprise server, a laptop computer, a notebook, a tablet computer, a netbook computer, a personal computer (PC), a desktop computer, a server, a personal digital assistant (PDA), a smart phone, a mobile phone, a virtual device, a thin client, an IoT device, or any other electronic device or computing system capable of sending and receiving data to and from other computing devices. While the smart device 120 is shown as a single device, in other embodiments, the smart device 120 may be comprised of a cluster or plurality of computing devices, in a modular manner, etc., working together or working independently. The smart device 120 is described in greater detail as a hardware implementation with reference to FIG. 3, as part of a cloud implementation with reference to FIG. 4, and/or as utilizing functional abstraction layers for processing with reference to FIG. 5.

The traumatic event detection client 122 may act as a client in a client-server relationship, e.g., with a traumatic event detection server 130, as well as a central hub for wirelessly receiving measurements from the sensors 110. The traumatic event detection client 122 may a software and/or hardware application capable of communicating with and providing a user interface for a user to interact with the traumatic event detection server and other computing devices via the network 108. Moreover, the traumatic event detection client 122 may be further capable of transferring data from the smart device 120 to and from other devices via the network 108. In embodiments, the traumatic event detection client 122 may utilize various wired and wireless connection protocols for data transmission and exchange, including Bluetooth, 2.4 gHz and 5 gHz internet, near-field communication (NFC), etc. The traumatic event detection client 122 is described in greater detail with respect to FIG. 2-5.

In exemplary embodiments, the traumatic event detection server 130 includes a traumatic event detection program 132, and may act as a server in a client-server relationship with the traumatic event detection client 122. The traumatic event detection server 130 may be an enterprise server, a laptop computer, a notebook, a tablet computer, a netbook computer, a personal computer (PC), a desktop computer, a server, a personal digital assistant (PDA), a smart phone, a mobile phone, a virtual device, a thin client, an IoT device, or any other electronic device or computing system capable of sending and receiving data to and from other computing devices. While the traumatic event detection server 130 is shown as a single device, in other embodiments, the traumatic event detection server 130 may be comprised of a cluster or plurality of computing devices, in a modular manner, etc., working together or working independently. The traumatic event detection server 130 is described in greater detail as a hardware implementation with reference to FIG. 3, as part of a cloud implementation with reference to FIG. 4, and/or as utilizing functional abstraction layers for processing with reference to FIG. 5.

The traumatic event detection program 132 may be a software and/or hardware program that may configure sensors and traumatic event detection. In addition, the traumatic event detection program 132 may collect environmental and biometric data via one or more sensors. The traumatic event detection program 132 may further determine whether a traumatic event is detected based on applying a model to the environmental and biometric data. Based on detecting a traumatic event, the traumatic event detection program 132 may estimate a TBI, a direction, and a magnitude of the detected traumatic event, as well as receive feedback and update the model.

Figure 2:
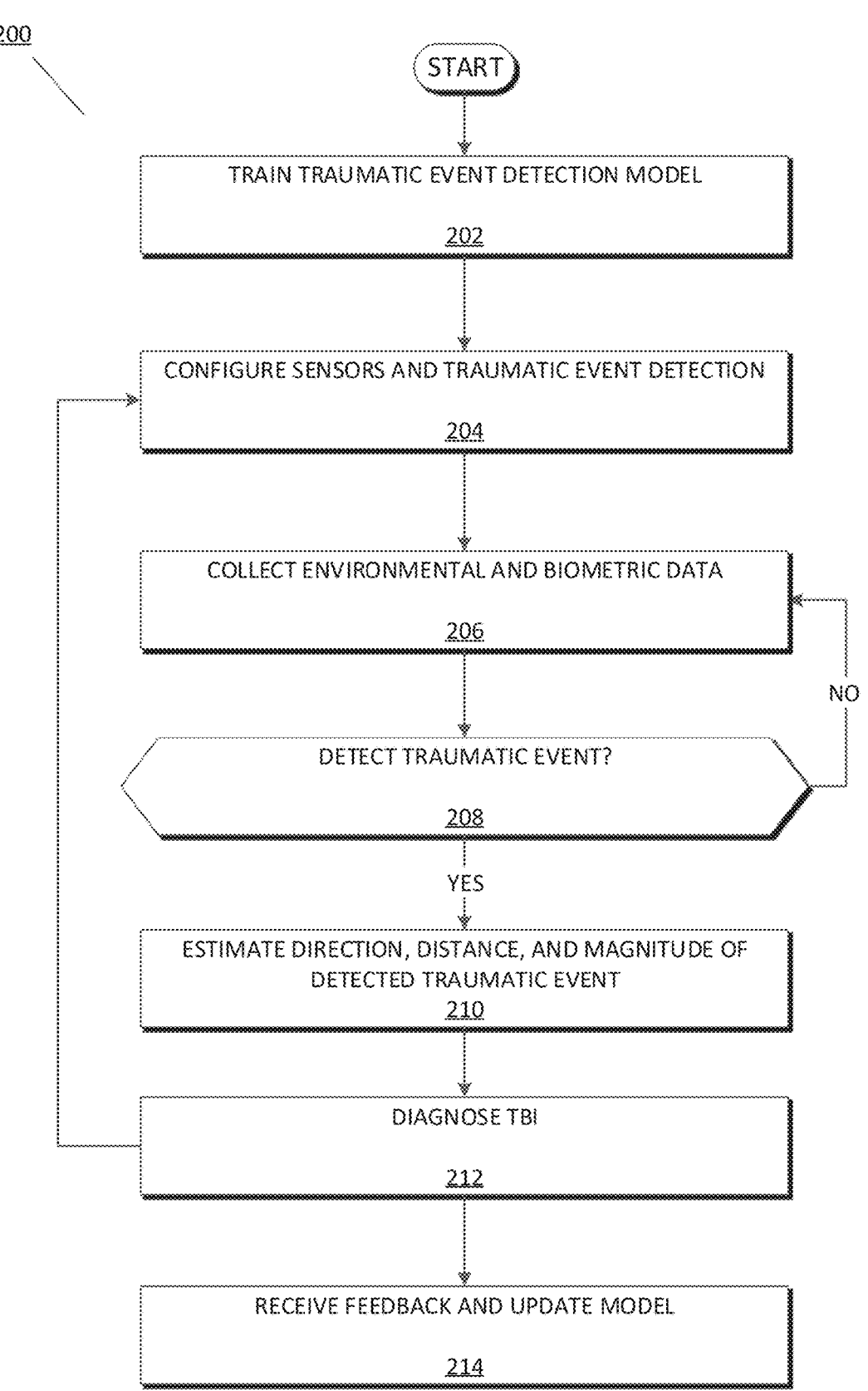
FIG. 2 depicts an exemplary flowchart 200 illustrating the operations of a traumatic event detection program 132 of the traumatic event detection system 100, in accordance with the exemplary embodiments.

FIG. 2 depicts an exemplary flowchart 200 illustrating the operations of the traumatic event detection program 132 of the traumatic event detection system 100, in accordance with the exemplary embodiments.

The traumatic event detection program 132 may train a traumatic event detection model (step 202). In embodiments, the traumatic event detection program 132 may be trained to detect traumatic events based on a model relating one or more traumatic events and a magnitude thereof with one or more measurements (or features) measured by the sensors 110 (collection of measurements described in greater detail forthcoming). The model may, e.g., be trained to identify a particular traumatic event based on comparing one or more specific feature measurements to one or more specific ranges.

In an example, an explosion may be detected based on pressure exceeding a threshold pounds per square inch, sounds exceeding a threshold decibel, temperature measurement exceeding a threshold temperature, acceleration exceeding a threshold, and GPS location change indicating high speed. In addition, the strain gauge and stress sensor in the contact lens can measure the amount of energy from pressure wave passing to a human body. Alternatively, detection may be triggered by one or more signals showing a rapid variation in time. In the blast wave example, there may be an abrupt rise in overpressure that is subthreshold, however when combined with a sudden change on the accelerometers is indictive of an event occurring. Conversely, the above explosion example may instead be indicative of a car crash when the model instead identifies a rapid drop in speed and lack of GPS location change. Furthermore, the car crash example may instead be indicative of a sporting impact when sound does not exceed a particular threshold. Overall, the model may store parameters most commonly associated with one or more traumatic events such that a traumatic event may be identified based one or more measurements from the sensors 110 alone.

Moreover, the model may associate particular measurements with a risk of a TBI or other injury suffered, allowing for a rapid initial diagnosis thereof based on remotely measured data alone. The model may be, e.g., a neural network trained using data labelled to associate traumatic events with corresponding sensor 110 measurements. In embodiments, a user may further enter into the model an activity, e.g., intensive sport, such that specific activities may be further correlated by the model with the TBIs and corresponding sensor 110 measurements.

In order to better illustrate the operations of the traumatic event detection program 132, reference is now made to an illustrative example where the traumatic event detection program 132 is implemented for a user as they drive to work in the morning.

The traumatic event detection program 132 may be configured (step 204). The traumatic event detection program 132 may be initially configured by first receiving user consent to collect data as well as registration information that may include, for example, log in credentials, internet protocol (IP) address, media access control (MAC) address, etc., via the traumatic event detection client 122 and the network 108. With respect to receiving user consent, the traumatic event detection client 122 may allow a user to manage the data collected and the manner in which the data may be collected, used, transferred, distributed, etc., as well as an option to opt out of such data collection. In any managing of user data, the traumatic event detection program 132 may be configured to adhere to at least all data handling and privacy protocols applicable. If desired, the configuration may further include selecting an activity performed by the wearer or use of the traumatic event detection system 100 in order better an accuracy of the TBI prediction, i.e., sporting, construction, leisure, etc.

In addition to receiving user consent, the traumatic event detection program 132 may further receive a configuration of the sensors 110. In embodiments, any number of the sensors 110 may be implanted, adhered to, and/or worn on the body in one or more positions, and each of the one or more sensors 110 may include various functionality. In embodiments, the sensors 110 may include wireless transceivers and comprise one or more of a smart contact lens worn in the eye, a smart earplug worn in the ear, and a smart adhesive patch worn on the body, all interconnected wirelessly via a hub (e.g., smart phone).

The smart contact lens may measure pressure, eye strain, stress, and movement (e.g., via a strain gauge), acceleration (e.g., via an accelerometer), and light (e.g., via a camera/light detector). Moreover, the smart contact lens may further analyse tears of a wearer to measure pH (e.g., via a pH sensor), ionic concentration (e.g., via ion-selective microelectrodes), enzyme (e.g., via spectrophotometry, fluorescence, and radiolabelling), etc. The smart earplug may measure sound (e.g., speech, level via a decibel meter), pressure (e.g., via a strain gauge), temperature (e.g., via a thermometer), etc. In addition, the smart adhesive patch may measure a pulse O2 (e.g., via a pulse oximetry sensor), heart rate (e.g., via a heart rate monitor), respiration rate (e.g., via a heartrate monitor), respiration (e.g., via a respiration monitor), skin conductance, GPS location, movement speed based on GPS location, etc.

The hub for wirelessly receiving measurements from the one or more sensors 110 may be located in, on, or near the body of the wearer, e.g., the smart device 120 operating as a smart phone. Configuration may additionally include establishing wireless communication between the smart device 120 acting as the hub and the sensors 110 (via, e.g., Bluetooth, NFC, etc.), as well as between the hub and the traumatic event detection server 130 (via, e.g., the internet). The sensors 110 may be positioned such that directional and magnitude data of a traumatic event may be calculated based on, e.g., comparing a magnitude of received data signals and a difference in time between received signals at two differently positioned sensors 110 (described in greater detail hereafter).

Returning to the aforementioned example, the user configures a smart phone (i.e. the smart device 120) to act as a communications hub and wears two smart contact lenses, two smart earplugs, and a smart adhesive patch adhered to their chest.

The traumatic event detection program 132 may collect data (step 206). In embodiments, the traumatic event detection program 132 may collect the data via communication with the sensors 110 via the network 108, e.g., Bluetooth or NFC. As previously described, the data extracted by, e.g., a smart lens, may include pressure, eye strain, stress, and movement (e.g., via a strain gauge), acceleration (e.g., via an accelerometer), and light (e.g., via a camera/light detector). The smart contact lens may further analyse tears of a wearer to measure pH (e.g., via a pH sensor), ionic concentration (e.g., via ion-selective microelectrodes), enzyme (e.g., via spectrophotometry, fluorescence, and radiolabelling), etc. The smart earplug may measure sound (e.g., via a decibel meter), pressure (e.g., via a strain gauge), temperature (e.g., via a thermometer), etc. In addition, the smart adhesive patch may measure a pulse O2 (e.g., via a pulse oximetry sensor), heart rate (e.g., via a heart rate monitor), respiration rate (e.g., via a heartrate monitor), respiration (e.g., via a respiration monitor), skin conductance, GPS location, movement speed based on GPS location, etc.

The cognitive assessments may be done by asking the wearer a prepared question or asking them to interpret a picture, e.g., using a speaker and/or display of the traumatic event detection client 122. The wearer response is recorded and analysed to assess cognitive measures. In addition, the traumatic event detection program 132 assess cognitive measures by asking the wearer to draw on the picture, e.g., identify objects, outline, etc., or to answer questions on a provided questionnaire. The measurements may be collected by the traumatic event detection program 132 via the smart device 120 acting as a smart phone and a wireless communication hub for aggregating measurements taken by the sensors 110. The data will also go through pre-processing steps to remove outliers, impute missing data, identify important features, etc.

Referencing the previously introduced illustrative example, the traumatic event detection program 132 collects light, strain and stress data from the smart eye lenses, acoustic and acceleration data from the smart earplugs, physiology data from the smart adhesive patch (or implant), and cognitive state assessments as descried above. In addition, the traumatic event detection program 132 records the times at which the measurements are detected at the relative sensor 110 positions.

The traumatic event detection program 132 may determine whether a traumatic event is detected based on the collected data (decision 208). The traumatic event detection program 132 may determine whether a traumatic event is detected based on applying the model to the measured sensor data. As previously described, the model may be trained to associate one or more measurements and one or more ranges thereof with one or more traumatic events and TBIs. In embodiments, the traumatic event detection program 132 may detect traumatic events based on comparing the measured features to thresholds and ranges correlated with traumatic events and TBIs as defined by the model previously generated. For example, the traumatic event detection program 132 may identify a traumatic event based on one or more measurements exceeding an absolute/relative threshold, and/or falling within a particular range of values. These thresholds and/or ranges may be defined by the model and adjusted through a feedback loop. When applying the model, the traumatic event detection program 132 may identify traumatic events based on identifying feature values that coincide/exceed/do not exceed with those associated with traumatic events by the model. In such embodiments, the measurements may need be taken within a brief temporal proximity of each other, e.g., milliseconds.

With reference again to the example above, the traumatic event detection program 132 detects a traumatic event based on detecting rapid changes in measurements of acceleration, strain, and speed.

If the traumatic event detection program 132 detects a traumatic event, the traumatic event detection program 132 may estimate direction, distance, and magnitude of the traumatic event (step 210). In embodiments, the traumatic event detection program 132 may be capable of determining at least one of a direction, distance, and magnitude of a detected traumatic event based on the relative locations of the sensors 110, magnitudes of the measurements, and the times at which the measurements were taken. For example, magnitude of and distance to a traumatic event may be deduced based on a measured strength of a signal. In addition, using a distance between the sensors 110 and a difference in time between measurements taken by the sensors 110, a speed of a blast, impact, etc. may be deduced. Similarly, and again based at on a distance between the sensors 110, the traumatic event detection program 132 may utilize a difference in measured magnitude between the sensors 110 in order to determine a distance from the traumatic event. An accuracy of the estimated direction, distance, and magnitude may be improved by increasing a distance between the sensors 110. Increasing a distance between the sensors 110 may be achieved by optimizing sensor placement or, when applicable, increasing a number of wearers of the traumatic event detection system 100.

With reference again to the formerly introduced example, the traumatic event detection program 132 may estimate a car crash of high magnitude at the immediate left side of the user.

The traumatic event detection program 132 may estimate a TBI (step 212). In exemplary embodiments, the traumatic event detection program 132 may estimate a TBI based on applying the model to the measured features. In particular, the traumatic event detection program 132 may estimate a TBI based on comparing the measured features to the ranges/thresholds indicative of a particular TBI as detailed by the model. The traumatic event detection program 132 may take further action based on identifying a TBI. Such further action may include calling for assistance locally or remotely, providing medical instructions for those who can help nearby, etc.

Continuing the earlier introduced example, the traumatic event detection program 132 diagnoses the user with a concussion based on comparing the feature measurements to those detailed by the model. The traumatic event detection program 132 may additionally call for an ambulance.

The traumatic event detection program 132 may receive feedback and update the model (step 214). The traumatic event detection program 132 may receive feedback in the form of user input, which may indicate whether the initially diagnosed TBI is confirmed by an administrator such as a doctor or medic. The feedback may, e.g., alter a feature, range, or weight thereof associated with a particular TBI in the model.

Concluding the aforementioned example, the traumatic event detection program 132 may, based on receiving feedback indicating that the correct diagnose was a concussion, update the model.

Figure 5:
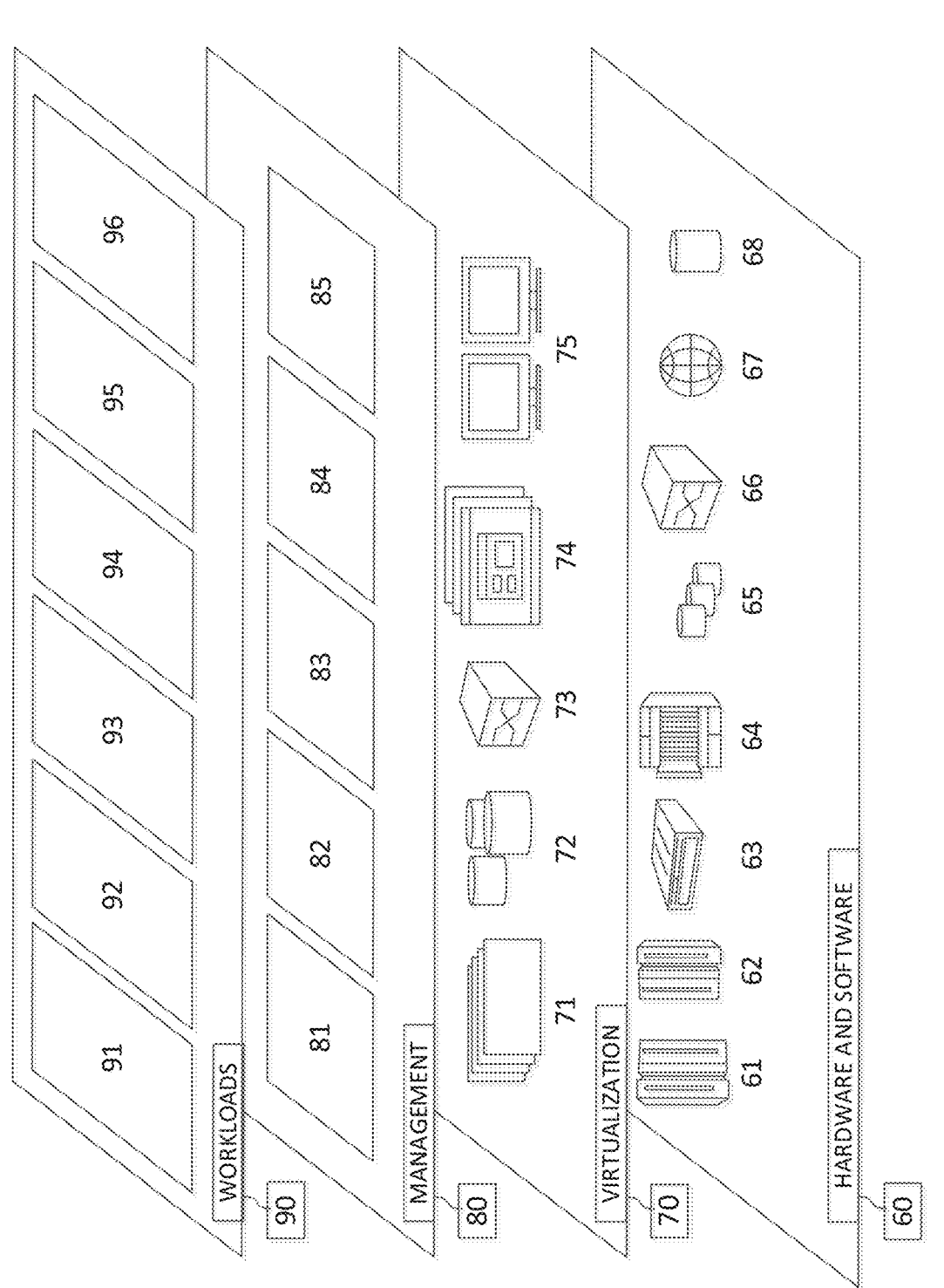
FIG. 5 depicts abstraction model layers, in accordance with the exemplary embodiments.

FIG. 3 depicts a block diagram of devices used within traumatic event detection system 100 of FIG. 1, in accordance with the exemplary embodiments. It should be appreciated that FIG. 5 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 4, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 40 and cloud computing environment 50 can communicate with any type of computerized device over any type of network and/or network addressable connection (e.g., using a web browser).

Referring now to FIG. 5, a set of functional abstraction layers provided by cloud computing environment 50 (FIG. 4) is shown. It should be understood in advance that the components, layers, and functions shown in FIG. 5 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and traumatic event processing 96.

The exemplary embodiments may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for traumatic event detection, the method comprising:
collecting data using sensors worn by a user, the sensors including micro-electromechanical system-based ultrafast switches;
identifying a traumatic brain injury based on applying a model to the data, wherein the model infers the traumatic brain injury of one or more traumatic brain injuries based on the data; and
determining a direction, a distance, and a magnitude relative to the user of a cause of the traumatic brain injury based on inputting relative locations of the sensors, magnitudes of the data collected, and times at which the data was collected into the model.

2. The computer-implemented method of claim 1, wherein the sensors are further selected from a group consisting of a contact lens, an earplug, a watch, an adhesive patch, an implantable device, and a smart device.

3. The computer-implemented method of claim 1, wherein the collected data is selected from a group consisting of accelerometer data, pressure data, stress data, strain data, pulse O2 data, heart rate data, respiration data, and skin conductivity data.

4. The computer-implemented method of claim 1, wherein the collected data further comprises cognitive assessment measures, and wherein the cognitive assessment measures are collected via the user completing a questionnaire, interpretation, or drawing.

5. The computer-implemented method of claim 1, wherein estimating the direction and the magnitude of the cause of the traumatic brain injury is based on differential signaling of the sensors on at least two of a front, a back, and a side of the user.

6. The computer-implemented method of claim 1, further comprising:
receiving feedback indicative of whether the identified traumatic brain injury was correctly identified, and
adjusting the model based on the received feedback.

7. A computer program product for traumatic event detection, the computer program product comprising:
one or more non-transitory computer-readable storage media and program instructions stored on the one or more non-transitory computer-readable storage media configured for:
collecting data using sensors worn by a user, the sensors including micro-electromechanical system-based ultrafast switches;

identifying a traumatic brain injury based on applying a model to the data, wherein the model infers the traumatic brain injury of one or more traumatic brain injuries based on the data; and determining a direction, a distance, and a magnitude relative to the user of a cause of the traumatic brain injury based on inputting relative locations of the sensors, magnitudes of the data collected, and times at which the data was collected into the model.

8. The computer program product of claim 7, wherein the sensors are further selected from a group consisting of a contact lens, an earplug, a watch, an adhesive patch, an implantable device, and a smart device.

9. The computer program product of claim 7, wherein the collected data is selected from a group consisting of accelerometer data, pressure data, stress data, strain data, pulse O2 data, heart rate data, respiration data, and skin conductivity data.

10. The computer program product of claim 7, wherein the collected data further comprises cognitive assessment measures, and wherein the cognitive assessment measures are collected via the user completing a questionnaire, interpretation, or drawing.

11. The computer program product of claim 7, wherein estimating the direction and the magnitude of the cause of the traumatic event is based on differential signaling of the sensors on at least two of a front, a back, and a side of the user.

12. The computer program product of claim 7, further comprising:

receiving feedback indicative of whether the identified traumatic brain injury was correctly identified, and adjusting the model based on the received feedback.

13. A computer system for traumatic event detection, the system comprising:

one or more computer processors, one or more computer-readable storage media, and program instructions stored on the one or more of the computer-readable storage media for execution by at least one of the one or more processors configured for:

collecting data using sensors worn by a user, the sensors including micro-electromechanical system-based ultrafast switches;

identifying a traumatic brain injury based on applying a model to the data, wherein the model infers the traumatic brain injury of one or more traumatic brain injuries based on the data; and determining a direction, a distance, and a magnitude relative to the user of a cause of the traumatic brain injury based on inputting relative locations of the sensors, magnitudes of the data collected, and times at which the data was collected into the model.

14. The computer system of claim 13, wherein the sensors are further selected from a group consisting of a contact lens, an earplug, a watch, an adhesive patch, an implantable device, and a smart device.

15. The computer system of claim 13, wherein the collected data is selected from a group consisting of accelerometer data, pressure data, stress data, strain data, pulse O2 data, heart rate data, respiration data, and skin conductivity data.

16. The computer system of claim 13, wherein the collected data further comprises cognitive assessment measures, and wherein the cognitive assessment measures are collected via the user completing a questionnaire, interpretation, or drawing.

17. The computer system of claim 13, wherein estimating the direction and the magnitude of the cause of the traumatic event is based on differential signaling of the sensors on at least two of a front, a back, and a side of the user.

* * * * *